United States Patent [19]
Hansenne et al.

[11] Patent Number: 5,866,148
[45] Date of Patent: Feb. 2, 1999

[54] PHOTOPROTECTIVE COMPOSITIONS COMPRISING MUTUALLY INCOMPATIBLE OILY DISPERSED PHASES

[75] Inventors: Isabelle Hansenne, Paris; Karine De Chabannes, Orleans; Sandrine Vernaire, Paris, all of France

[73] Assignee: Société L'oréal S.A., Paris, France

[21] Appl. No.: 880,739

[22] Filed: Jun. 23, 1997

[30] Foreign Application Priority Data

Jun. 21, 1996 [FR] France .................................. 96 07775

[51] Int. Cl.⁶ .................................................. A61K 7/42
[52] U.S. Cl. .............................. 424/401; 424/59; 424/60; 424/70.1; 514/937
[58] Field of Search ................................ 424/401, 59, 60, 424/70.12, 70.1; 514/492, 494, 502, 937, 938, 941

[56] References Cited

U.S. PATENT DOCUMENTS

| | | | |
|---|---|---|---|
| 5,658,555 | 8/1997 | Ascione et al. | 424/59 |
| 5,670,139 | 9/1997 | Allard et al. | 424/59 |
| 5,679,374 | 10/1997 | Franchon et al. | 424/450 |
| 5,691,380 | 11/1997 | Mason et al. | 514/562 |

FOREIGN PATENT DOCUMENTS

| | | |
|---|---|---|
| 0552024 | 7/1993 | European Pat. Off. . |
| 0685228 | 12/1995 | European Pat. Off. . |
| 96/14076 | 5/1996 | WIPO . |

*Primary Examiner*—Thurman K. Page
*Assistant Examiner*—Lakshmi S. Channavajjala
*Attorney, Agent, or Firm*—Burns, Doane, Swecker & Mathis, L.L.P.

[57] ABSTRACT

Topically applicable, water resistant cosmetic/dermatological compositions well suited for enhanced photoprotection of human skin and or/hair against the damaging effects of UV-A and UV-B irradiation, particularly solar radiation, comprise (I) a continuous aqueous dispersing phase, (ii) a first discontinuous globular oily dispersed phase $O_1$, (iii) a second discontinuous globular oily dispersed phase $O_2$, (iv) at least one O/W emulsifying agent, (v) at least one W/O emulsifying agent, (vi) a photoprotecting effective amount of at least one lipophilic UV screening agent, (vii) a photoprotecting effective amount of at least one hydrophilic screening agent, said first and second oily phases $O_1$ and $O_2$ being mutually incompatible, and the globules constituting said oily phase $O_1$ having an average size which is different from the globules constituting said oily phase $O_2$.

28 Claims, No Drawings

PHOTOPROTECTIVE COMPOSITIONS COMPRISING MUTUALLY INCOMPATIBLE OILY DISPERSED PHASES

BACKGROUND OF THE INVENTION

1. Technical Field of the Invention

The present invention relates to the formulation of novel cosmetic/dermatological compositions for topical application, for the photoprotection of the skin and/or the hair against ultraviolet radiation, in particular solar radiation, these novel compositions (hereinafter sometimes referred to simply as "sunscreen" or "antisun" compositions) having an improved SPF and an improved resistance to removal by water.

2. Description of the Prior Art

It is known to this art that light radiation of wavelengths of from 280 nm to 400 nm promotes tanning of the human epidermis, and that irradiation of wavelengths of from 280 nm to 320 nm, i.e., UV-B irradiation, causes skin burns and erythema which may be harmful to the development of a natural tan; hence, this UV-B radiation should be screened from the skin.

It is also known to this art that UV-A radiation, of wavelengths of from 320 nm to 400 nm, which causes tanning of the skin, also adversely affects it, especially in the case of sensitive skin or of skin which is continually exposed to solar radiation. UV-A rays cause, in particular, a loss of elasticity of the skin and the appearance of wrinkles, promoting premature skin aging. Such irradiation promotes triggering of the erythemal reaction or enhances this reaction in certain individuals and may even be the cause of phototoxic or photoallergic reactions. It is thus desirable to also screen out UV-A radiation.

A wide variety of cosmetic and/or dermatological compositions intended for the photoprotection (UV-A and/or UV-B) of the skin are known to this art.

These antisun compositions are quite often formulated as an emulsion of oil-in-water type (namely, a cosmetically and/or dermatologically acceptable vehicle, carrier or diluent comprising a continuous aqueous dispersing phase and a discontinuous oily dispersed phase) or of water-in-oil type (aqueous dispersed phase in a continuous oily phase) which contains, in various concentrations, one or more conventional lipophilic and/or hydrophilic organic photoscreening agents which are capable of selectively absorbing harmful or deleterious UV radiation. These screening agents (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent). In such emulsions, the hydrophilic screening agents are present in the aqueous phase and the lipophilic screening agents are present in the fatty phase.

Oil-in-water emulsions are generally more appreciated by consumers than water-in-oil emulsions, in particular on account of their pleasant feel (similar to water) and their presentation in the form of a non-greasy cream or milk. However, they also more readily lose their anti-UV protective efficacy as soon as they come into contact with water. The reason for this is that hydrophilic screening agents, in particular acidic such species, disappear in water, as a result of swimming in seawater or in a swimming pool, under the shower or while engaged in nautical sports. Thus, the antisun compositions comprising same, alone or combined with other lipophilic screening agents, no longer provide the desired initial protection once the substrate (skin or hair) on which they have been applied is contacted with water, this loss of protection factor by removal of the hydrophilic screening agent with water being all the more pronounced since the lipophilic/hydrophilic screening combination present in the composition is synergistic at the sun protection factor level.

Sunscreen compositions having improved SPFs and improved water-resistance may be provided as water-in-oil emulsions. This because a hydrophilic screening agent is more resistant to water in a water-in-oil emulsion than in an oil-in-water emulsion. However, as indicated above, such compositions are still not entirely satisfactory, insofar as after they have been applied, the user still experiences a particularly unpleasant sensation of greasiness.

It is also known to this art to improve the SPF of antisun/sunscreen emulsions, in particular oil-in-water emulsions, containing one or more hydrophilic screening agents by combining these sunscreens with certain very specific lipophilic screening agents, as described, for example, in EP-A-0,685,228, assigned to the assignee hereof. However, according to that technique, the improvements in the SPF obtained are based on the synergistic combination of specific hydrophilic and lipophilic screening agents (such as benzene-1,4-di(3-methylidene-10-camphorsulfonic) acid and 2-ethylhexyl α-cyano-β,β-diphenylacrylate in the case of EP-A-0,685,228) in standard oil-in-water emulsions, such that these improvements cannot be obtained generally, namely, irrespective of the hydrophilic and lipophilic screening agent(s) employed.

Thus, need continues to exist in this art for antisun/sunscreen compositions comprising both at least one hydrophilic screening agent and at least one lipophilic screening agent, and whose SPF is high and stable over time, irrespective of the hydrophilic and/or lipophilic screening agent(s) employed.

SUMMARY OF THE INVENTION

According, a major object of the present invention is the provision of a unique technique for the formulation of novel antisun/sunscreen compositions containing at least one hydrophilic screening agent and at least one lipophilic screening agent, such novel compositions having, for a similar screening system [hydrophilic screening agent(s)+lipophilic screening agent (s)], improved properties with respect to the compositions of the prior art containing standard oil-in-water or water-in-oil vehicles, diluents or carriers, in particular as regards the SPFs obtained and their stability, especially resistance to removal by water.

DETAILED DESCRIPTION OF BEST MODE AND SPECIFIC/PREFERRED EMBODIMENTS OF THE INVENTION

More particularly according to the present invention, the standard technique for formulating emulsions in general, and antisun/sunscreen emulsions comprising lipophilic and hydrophilic screening agents in particular, is well known to this art.

Such technique entails preparing, under hot conditions (generally at about 80°) and with stirring, a fatty phase A containing at least one emulsifying agent, optionally a coemulsifying agent, at least one oil, the lipophilic screening agent or agents and optionally one or more other fatty substances. An aqueous phase B comprising the hydrophilic screening agent or agents and water, and optionally one or more hydrating agents, is prepared separately, this phase being heated to the same temperature as that of the fatty phase, and homogenized by simple stirring. These two phases A and B are then mixed together, with stirring, in order to produce an emulsion which is permitted to cool, again with stirring. Lastly, a third phase C which comprises a thickener may optionally be added.

Standard antisun/sunscreen emulsions are thus prepared, either of oil-in-water type or water-in-oil type depending on the nature of the HLB (hydrophilic-lipophilic balance) of the emulsifying system selected.

Such a standard technique does not permit obtaining antisun/sunscreen compositions which are comparable in performance with those according to the present invention.

Briefly, the present invention features a novel technique for the formulation of antisun/sunscreen emulsions which makes it possible to obtain novel compositions having improved properties, in particular as regards the SPFs associated therewith. Even more especially, it has surprisingly and unexpectedly been found that the prior preparation of a phase comprising all of the hydrophilic and lipophilic screening agents, followed by the addition of this phase to a pre-prepared emulsion, provides novel compositions which exhibit particularly good performance as regards both the SPF value itself and the stability over time of this SPF, and in particular its resistance to removal by water.

Thus, the present invention features a novel process for the preparation of photoprotective compositions comprising, in a cosmetically and/or dermatologically acceptable vehicle, diluent or carrier of mixed oil-water type, at least one lipophilic screening agent and at least one hydrophilic screening agent, and which comprises introducing, into an oil-in-water emulsion obtained by mixing (i) an aqueous phase A and (ii) an oily phase $O_1$ comprising an O/W emulsifying agent, an oily phase $O_2$ comprising a W/O emulsifying agent, the said lipophilic screening agent and the said hydrophilic screening agent, and the said oily phases $O_1$ and $O_2$ being mutually incompatible.

Such process enables the provision of novel compositions simultaneously comprising a hydrophilic screening agent and a lipophilic screening agent and which have an SPF which is particularly high and, in any event, higher than that of photoprotective compositions containing the same screening system in a different vehicle.

The present invention also features novel photoprotective cosmetic and/or dermatological compositions, per se, characteristically prepared by the process described above and which comprise:

(i) a continuous aqueous dispersing phase, (ii) a first discontinuous oily dispersed phase $O_1$, (iii) a second discontinuous oily dispersed phase $O_2$, (iv) at least one O/W emulsifying agent, (v) at least one W/O emulsifying agent, (vi) at least one lipophilic screening agent, (vii) at least one hydrophilic screening agent, said first and second oily phases $O_1$ and $O_2$ being mutually incompatible, and the globules constituting said oily phase $O_1$ having an average size which is different from the globules constituting said oily phase $O_2$.

Other than their conspicuous efficacy as regards the photoprotection of human skin and/or hair, the compositions according to the invention also have a very good retention of the SPF to water. Stated differently, the hydrophilic screening agents which they contain are entrained very little by water and the compositions remain effective even after swimming in the ocean or in a swimming pool, for example.

This invention also features a cosmetic treatment regime for protecting the skin and/or the hair against ultraviolet radiation, in particular solar radiation, comprising topically applying an effective amount of a composition as described above to the skin and/or the hair.

Too, this invention also features the use of the compositions as described above as, or for the production of, cosmetic/dermatological compositions for protecting the skin and/or the hair against ultraviolet radiation, in particular solar radiation.

The first step of the process according to the invention comprises preparing an oily phase $O_1$ in conventional manner. This phase comprises at least one O/W emulsifying agent. For the purposes of the present invention and in the description which follows, the term O/W emulsifying agent connotes any compound or agent having emulsifying properties which permits the preparation of oil-in-water emulsions. Exemplary O/W emulsifying agents according to the present invention, include the O/W emulsifying agents typically employed in the preparation of standard oil-in-water emulsions, such as fatty acid esters of polyethylene glycol (PEG), fatty acid esters of glycerol (glyceryl stearate) or fatty acid esters of sugar (sorbitan stearate), as well as the polyoxyethylenated or polyoxypropylenated derivatives thereof, sugar ethers, anionic surfactants (K or Na alkyl phosphate) and polyalkoxylated fatty alcohols.

Exemplary fatty-chain polymers having emulsifying properties and useful for preparing oil-in-water emulsions include, for example, the acrylic acid/C10–C30 alkyl acrylate copolymer marketed under the trademark "Pemulen TR-1" by Goodrich.

An O/W emulsifying agent which is particularly preferred according to the present invention is the mixture of glyceryl mono/distearate and polyethylene glycol stearate (100 EO) marketed under the trademark "Arlacel 165" by ICI.

The O/W emulsifying agent is advantageously present in the final cosmetic/dermatological compositions according to the invention in amounts which may range from 0.1% to 10%, preferably from 0.1% to 5%, by weight relative to the total weight of the composition.

This first oily phase $O_1$ may also comprise a coemulsifying agent intended to impart consistency to the emulsion. The coemulsifying agents may be selected, for example, from between stearyl alcohol and stearic acid.

The first oily phase also comprises one or more fatty substances, it being possible for these fatty substances to be an oil or a wax or mixtures thereof. By the term "oil" is intended a compound which is liquid at room temperature. By the term "wax" is intended a compound which is solid or substantially solid at room temperature and whose melting point is generally above 35° C.

Oils which are representative are mineral oils (petrolatum); plant oils (sweet almond oil, macadamia oil, blackcurrant seed oil, jojoba oil); synthetic oils such as perhydrosqualine, fatty alcohols, acids or esters (such as the C12–C15 alkyl benzoate marketed under the trademark "Finsolv TN" by Finetex, octyl palmitate, isopropyl lanolate, triglycerides including those of capric/caprylic acids), oxyethylenated or oxypropylenated fatty esters and ethers; silicone oils (cyclomethicone, polydimethylsiloxanes or PDMSs) or fluoro oils, and polyalkylenes.

Waxy compounds which are representative are paraffin, carnauba wax, beeswax and hydrogenated castor oil.

This first oily phase $O_1$ is generally prepared in a conventional manner by mixing the various constituents with simple stirring under hot conditions. This mixing may be carried out at a temperature of about 80° C., for example.

This oily phase $O_1$ is preferably free or devoid of any screening agent, in particular of any liposoluble screening agent.

A second step of the process according to the invention comprises preparing an aqueous phase in conventional manner. This phase generally comprises one or more hydrating agents and water. It may also comprise other hydrophilic constituents usually formulated into cosmetic and/or dermatological compositions.

This aqueous phase is generally prepared in a conventional manner by mixing together the various constituents with simple stirring under hot conditions. This mixing may be carried out at a temperature of about 80° C., for example.

This aqueous phase is preferably free or devoid of any screening agent, in particular of any water-soluble screening agent.

According to a third, essential step of the process according to the invention, a second oily phase $O_2$ is prepared separately from the aqueous phase and oily phase $O_1$, this phase $O_2$ comprising at least one W/O emulsifying agent, at least one hydrophilic screening agent and at least one lipophilic screening agent.

For the purposes of the present invention and in the description which follows, the term W/O emulsifying agent connotes any compound or agent having emulsifying properties which enables preparation of water-in-oil emulsions.

Exemplary W/O emulsifying agents which may be used for the preparation of the oily phase $O_2$ of the process according to the present invention include, in particular, dimethicone copolyols and their esters, such as the dimethicone copolyols marketed under the trademarks "Silicone $Q_2$ 5220", "Silicone DC 193" or "Silicone $Q_2$ 3225C" by Dow Corning. A dimethicone which is particularly preferred according to the present invention is that marketed under the trademark "Silicone $Q_2$ 3225C" by Dow Corning.

The W/O emulsifying agent is advantageously present in the final cosmetic/dermatological compositions according to the invention in amounts which may range from 0.1% to 10%, preferably from 0.1% to 5%, by weight relative to the total weight of the composition.

An essential characteristic of the present invention is the presence in this phase $O_2$ of one or more hydrophilic sunscreens which are active in the UV-A and/or UV-B region (absorbers). This or these hydrophilic screening agents are advantageously selected from among the benzophenone derivatives, p-aminobenzoic acid derivatives, camphor derivatives and benzimidazole derivatives.

Particularly exemplary hydrophilic screening agents according to the present invention include benzene-1,4-di(3-methylidene-10-camphorsulfonic) acid and 2-phenylbenzimidazole-5-sulfonic acid marketed under the trademark "Eusolex 232" by Merck.

The hydrophilic screening agent or agents are advantageously present in the final cosmetic/dermatological compositions according to the invention in amounts which may range from 0.1% to 20%, preferably from 0.2% to 10%, by weight relative to the total weight of the composition.

According to another essential characteristic of the present invention, the oily phase $O_2$ also comprises at least one lipophilic sunscreen which is active in the UV-A and/or UV-B region. Lipophilic screening agents which are particularly suitable for the present invention may be selected from among dibenzoylmethane derivatives, benzimidazole derivatives, cinnamic derivatives, salicylic derivatives, camphor derivatives, triazine derivatives, benzophenone derivatives, β,β-diphenylacrylate derivatives, p-aminobenzoic acid derivatives and the screening polymers and screening silicones described in WO-93/04665 and WO-94/06404. Other examples of organic screening agents are set forth in EP-A-0,487,404.

Particularly exemplary lipophilic screening agents according to the present invention include 4-tert-butyl-4'-methoxydibenzoylmethane marketed under the trademark "Parsol 1789" by Givaudan and 2-ethylhexyl α-cyano-β,β-diphenylacrylate marketed under the trademark "Uvinul N 539" by BASF.

The lipophilic screening agent or agents are advantageously present in the final cosmetic/dermatological compositions according to the invention in amounts which may range from 0.5% to 30%, preferably from 0.5% to 20%, by weight relative to the total weight of the composition.

Preferably, the oily phase $O_2$ comprises all of the hydrophilic and lipophilic UV-A and/or UV-B screening agent(s) sought to be formulated into the final compositions according to the invention.

This oily phase $O_2$ also comprises one or more fatty substances selected from among those indicated above for the preparation of the oily phase $O_1$, such that the oily phases $O_1$ and $O_2$ are incompatible in the composition. Preferably, this fatty substance is a volatile silicone oil, such as cyclomethicones, or a non-volatile silicone oil, such as dimethicones. Preferably also, a volatile silicone oil such as, for example, the cyclomethicones marketed under the trademarks "DC 245 Fluid" or "DC 246 Fluid" by Dow Corning is used in the present invention.

This silicone oil is advantageously present in the final cosmetic/dermatological compositions according to the invention in amounts which may range from 1% to 20%, preferably from 2% to 10%, by weight relative to the total weight of the composition.

The fourth step of the process according to the invention comprises preparing an oil-in-water emulsion by introducing, with standard stirring, the first oily phase $O_1$ into the aqueous phase prepared in the second step.

The fifth step of the process of the invention comprises incorporating the oily phase $O_2$ thus prepared into the emulsion. This step may be carried out by simple stirring without any specific apparatus. After mixing, the composition is permitted to cool at room temperature.

The final compositions obtained according to the process in accordance with the invention thus comprise a continuous aqueous dispersing phase and two discontinuous oily dispersed phases $O_1$ and $O_2$, these two oily phases being mutually incompatible and thus separate, the globules constituting the oily phase $O_1$ having an average size which differs from that of the globules constituting the oily phase $O_2$, as well as lipophilic and hydrophilic screening agent(s).

The coexistence of two populations of oil globules with different sizes may thus be distinguished in the compositions in accordance with the invention, namely, a first population of oil globules whose size advantageously ranges from 1 to 10 μm and a second population formed of much finer oil globules, advantageously smaller than 1 μm in size.

According to all probability, the large globules correspond to the oily phase $O_2$ and the small globules to the oily phase $O_1$.

The cosmetic and/or dermatological compositions according to the invention may also contain coated or uncoated metal oxide pigments or nanopigments (average size of the primary particles: generally between 5 nm and 100 nm, preferably between 10 and 50 nm) such as, for example, nanopigments of titanium dioxide (amorphous or crystallized in rutile and/or anatase form), of iron oxide, of zinc oxide, of zirconium oxide or of cerium oxide which are all well-known photoprotective agents, per se, that act by physically blocking (reflection and/or diffusion) the UV radiation. Standard coating agents are, moreover, alumina and/or aluminum stearate, and silicones. Such coated or uncoated metal oxide nanopigments are described, in particular, in EP-A-0,518,772 and EP-A-0,518,773.

The nanopigments are advantageously present in the final cosmetic/dermatological compositions according to the invention in amounts which may range from 0.1% to 20%, preferably from 0.2% to 10%, by weight relative to the total weight of the composition.

The compositions according to the invention may also contain thickeners/thickening agents.

The thickeners are advantageously selected from among crosslinked polyacrylic acids, fatty-chain polyacrylic acids and modified or unmodified guar gums and cellulose gums such as hydroxypropyl guar gum, methylhydroxyethylcellulose and hydroxypropylmethyl cellulose.

The thickener or thickeners is/are typically present in the final compositions according to the invention in an amount ranging from 0.1% to 10%, preferably from 0.1% to 5%, by weight relative to the total weight of the composition.

This or these thickeners may be formulated into the compositions of the present invention either before or after step (5) of incorporating the oily phase $O_2$.

The compositions of this invention may also contain agents for the artificial tanning and/or browning of the skin (self-tanning agents) such as, for example, dihydroxyacetone (DHA).

The compositions in accordance with the present invention may also comprise standard cosmetic and/or dermatological adjuvants and additives, for example organic solvents, softeners, antioxidants, anti-free-radical agents, opacifiers, stabilizers, emollients, α-hydroxy acids, anti-foaming agents, hydrating agents, vitamins, fragrances, preservatives, surfactants, fillers, sequestering agents, polymers, propellants, basifying or acidifying agents, dyes, colorants or any other ingredient typically employed in the cosmetic and/or dermatological arts, in particular for the manufacture of sunscreen compositions in the form of emulsions.

The cosmetic and/or dermatological compositions of the invention are useful for protecting the human epidermis or hair against ultraviolet irradiation, as sunscreen composition or as makeup products.

In order to further illustrate the present invention and the advantages thereof, the following specific examples are given, it being understood that same are intended only as illustrative and in nowise limitative.

EXAMPLE 1

The following three emulsions were prepared: an emulsion (I) in accordance with the invention and prepared according to the process of the invention; an emulsion (II) comprising the same screening system as the emulsion (I) but prepared according to a standard process for preparing oil-in-water emulsions; and the emulsion (III) comprising the same screening system as the emulsions (I) and (II), but which was a water-in-oil emulsion.

The compositions of the formulations are given below (the amounts are expressed as a percentage by weight relative to the total weight of the composition):

| Emulsion (I) (Invention): | |
|---|---|
| $A_1$: | |
| Stearic acid | 1.5% |
| Glyceryl mono/distearate/polyethylene glycol stearate mixture (100 EO) marketed under the trademark "Arlacel 165" by ICI (O/W emulsifying agent) | 1.5% |
| Stearyl alcohol | 0.5% |
| Preservative | qs |
| Vinylpyrrolidine/eicosine copolymer marketed under the trademark "Antaron V220" by ISP | 1% |
| $A_2$: | |
| Triethanolamine | 0.45% |
| $B_1$: | |
| 4-Tert-butyl-4'-methoxydibenzoylmethane marketed under the trademark "Parsol 1789" by Givaudan (lipophilic screening agent) | 2% |
| 2-Ethylhexyl α-cyano-β,β-diphenylacrylate marketed under the trademark "Uvinul N 539" by BASF (lipophilic screening agent) | 10% |
| $B_2$: | |
| Polydimethylsiloxane marketed under the trademark "Silicone $Q_2$3225C" by Dow Corning (W/O emulsifying agent) | 1% |
| Cyclohexadimethylsiloxane marketed under the trademark "DC 246 Fluid" by Dow Corning | 5% |
| $B_3$: | |
| Benzene-1,4-di(3-methylidene-10-camphor sulfonic)acid (hydrophilic screening agent) | 1.5% (0.5% AM) |
| Triethanolamine | 0.26% |
| C: | |
| Potassium hexadecyl phosphate marketed under the trademark "Amphisol K" by Roche | 1% |
| D: | |
| Titanium dioxide nanopigment marketed under the trademark "MT100T" by Tayca | 5% |
| E: | |
| Hydrating agents | 15% |
| Preservative | qs |
| Sequestering agent | 0.1% |
| F: | |
| Polyacrylic acid marketed under the trademark "Carbopol 980" by Goodrich | 0.3% |
| $C_{12}/C_{15}$ alkyl benzoate marketed under the trademark "Finsolv TN" by Stéarineries Dubois | 2% |
| G: | |
| Triethanolamine | 0.3% |
| J: | |
| Purified water | qs 100% |

Procedure:
(a) Preparation of the oily phases $O_1$ and $O_2$ and of the aqueous phase according to the invention:
  (1) Preparation of phase $O_1$ according to the invention (oily phase containing the O/W emulsifying agent):
    $A_1$ was melted at 80° C. and, with stirring, $A_2$ was then added thereto.
  (2) Preparation of the aqueous phase:
    E was dissolved in J at 80° C. C was then added.
  (3) Preparation of phase $O_2$ according to the invention (oily phase comprising the screening agents and the W/O emulsifying agent):
    $B_1$ was heated to 70° C. $B_1$ was then introduced slowly into $B_2$ with turbo-mixing (a creamy white mixture was obtained). The mixture was cooled to 40° C. with stirring. Lastly, $B_3$ was incorporated very slowly into the mixture obtained.

(b) Formulation of the final composition:

The oily phase $O_1$ was introduced, at 75° C., into the aqueous phase with stirring. D was then introduced at about 70° C. F (prepared beforehand by dispersing the Carbopol 980 in the Finsolv TN with stirring under cold conditions) was introduced at about 60° C. The mixture was then neutralized by adding G. It was cooled to 40° C. Lastly, the oily phase $O_2$ was introduced with stirring into the $O_1$/W emulsion thus obtained. The mixture was cooled to 20° C.

Emulsion (II) (Comparative: standard oil-in-water emulsion)

The composition of emulsion (II) was the same as that of emulsion (I), but contained no phase $B_2$.

Procedure:

The oily phase $(A_1+A_2)$ was prepared as in Example 1; $B_1$ was then introduced therein.

Separately, E was dissolved in J at 80° C. in a tank; C was then added, followed by $B_3$. The oily phase $(A_1+A_2+B_1)$ prepared beforehand was added, at 75° C. with stirring, to this aqueous phase in order to obtain an O/W emulsion.

D was introduced at about 70° C. F (prepared beforehand by dispersing the Carbopol 980 in the Finsolv TN with stirring under cold conditions) was introduced at about 60° C. The mixture was then neutralized by adding G. Lastly, it was cooled to 20° C.

| Emulsion (III) (Comparative: standard water-in-oil emulsion): | |
|---|---|
| $A_1$: | |
| Polymethyllauryl/methylsiloxane EO and PO marketed under the trademark "DC $Q_2$ 5200" by Dow Corning | 2.5% |
| Cyclohexadimethylsiloxane marketed under the trademark "DC 246 Fluid" by Dow Corning | 8% |
| Isopropyl palmitate | 7% |
| Polydimethylsiloxane containing behenate groups, marketed under the trademark "Mirasil wax -B" by Rhône-Poulenc | 1% |
| $A_2$: | |
| 4-Tert-butyl-4'-methoxydibenzoylmethane marketed under the trademark "Parsol 1789" by Givaudan | 2% |
| 2-Ethylhexyl α-cyano-β,β-diphenylacrylate marketed under the trademark "Uvinul N 539" by BASF | 10% |
| B: | |
| NaCl | 2% |
| Hydrating agents | 8% |
| C: | |
| Benzene-1,4-di(3-methylidene-10-camphor sulfonic)acid | 1.5% (0.5% AM) |
| Triethanolamine | 0.26% |
| D: | |
| Titanium dioxide nanopigment marketed under the trademark "MT100T" by Tayca | 5% |
| E: | |
| Purified water | qs 100% |

Procedure:

$A_1$ free of the silicone "DC 246 Fluid" was heated to 60° C. It was cooled to 40° C. and the silicone "DC 246 Fluid" was then added. $A_2$ was then heated to 60° C. It was cooled to 40° C. $A_1$ and $A_2$ were mixed together. Separately, the mixture (B+E) was heated to 60° C. It was cooled to 40° C. and was then introduced, with stirring, into the phase $(A_1+A_2)$ in order to prepare the emulsion. D was then introduced into this emulsion with stirring. C was next introduced with stirring. Lastly, the mixture was cooled to 25° C.

Evaluation of the SPF of the Compositions Obtained

For each of the formulations (I), (II) and (III) thus prepared, the sun protection factor (SPF) associated therewith was then determined. The sun protection factor was measured according to the following technique (in vivo): these formulations were applied, at a rate of 2 mg of product/cm$^2$ of skin, onto the backs of 5 human models and the protected regions and unprotected regions of skin were then simultaneously subjected to the action of a sunlight simulator marketed under the trademark "Xenon Multiport WG 320-UG 11"; the sun protection factor (SPF) was then calculated mathematically by the ratio of the irradiation time which was necessary to reach the erythema-forming threshold with the UV screening agent (protected region) to the time which was necessary to reach the erythema-forming threshold without UV screening agent (unprotected region).

The 5 models were then instructed to take two baths in water, each bath lasting 20 minutes and the two baths being separated by an interval of 20 minutes.

The SPF was then determined again according to the same procedure as above.

The SPF results before and after the two baths are reported in Table I below:

TABLE (I)

| | SPF before the bath | SPF after the bath |
|---|---|---|
| Emulsion (I) (Invention) | 59.4 | 38.9 |
| Emulsion (II) (Comparative) | 34.0 | 10.5 |
| Emulsion (III) (Comparative) | 31.9 | 17.4 |

These results clearly evidence that, for an identical screening system, the emulsion (I) in accordance with the present invention had an SPF which was, on the one hand, particularly high and, on the other, remarkably water-resistant. In particular, even after two baths, the SPF of the emulsion according to the invention was much higher than that determined for a water-in-oil emulsion having an identical screening system (emulsion (III)).

EXAMPLE 2

This example compares two emulsions that were rigorously identical in composition but prepared according to two different procedures.

In this example, emulsion (I) of Example 1 and emulsion (II) of Example 1 were thus used again, emulsion (II) this time comprising the phase $B_2$; this emulsion is referred to hereinbelow as emulsion (II'). Emulsions (I) and (II') thus had exactly the same composition. Emulsion (I) was formulated according to the process in accordance with the invention described in Example 1. Emulsion (II') was formulated according to the standard technique for preparing the emulsion (II) of Example 1 (O/W emulsion), by incorporating phase $B_2$ into the oily phase when this oily phase was prepared.

The in vitro SPF was then evaluated for each of these two emulsions (I) and (II'). This was determined via the in vitro technique described by B. L. Diffey et al. in *J. Soc. Cosmet. Chem.*, 40, 127–133 (1989); this technique entails determining the monochromatic protection factors every 5 nm over a wavelength range from 290 to 400 nm and in calculating from the latter the sun protection factor according to a given mathematical equation.

The results (average value corresponding to five tests) are reported in Table II below:

TABLE (II)

|     | Emulsion (I) (Invention) | Emulsion (II') (Comparative) |
| --- | --- | --- |
| SPF | 70.4 | 56.2 |

These results clearly evidence that, for a rigorously identical composition, the emulsion formulated according to the process in accordance with the invention (emulsion (I)) had a much higher SPF than that formulated by a standard process for preparing O/W emulsion (emulsion (II')).

EXAMPLE 3

Another specific example of a sunscreen composition in the form of a cream-gel is set forth below.

| $A_1$: | |
| --- | --- |
| Acrylic acid/C10–C30 alkyl acrylate copolymer marketed under the trademark "Pemulen TR-1" by Goodrich | 0.4% |
| $A_2$: | |
| Triethanolamine | 0.4% |
| $B_1$: | |
| 4-Tert-butyl-4'-methoxydibenzoylmethane marketed under the trademark "Parsol 1789" by Givaudan | 2% |
| 2-Ethylhexyl α-cyano-β,β-diphenylacrylate marketed under the trademark "Uvinul N 539" by BASF | 10% |
| $B_2$: | |
| Polydimethylsiloxane marketed under the trademark "Silicone $Q_2$3225C" by Dow Corning | 1% |
| Cyclohexadimethylsiloxane marketed under the trademark "DC 246 Fluid" by Dow Corning | 5% |
| $B_3$: | |
| Benzene-1,4-di(3-methylidene-10-camphor sulfonic)acid | 1.5% (0.5% AM) |
| Triethanolamine | 0.26% |
| C: | |
| Titanium dioxide nanopigment marketed under the trademark "MT100T" by Tayca | 5% |
| D: | |
| Hydrating agents | 8% |
| Preservative | qs |
| Sequestering agent | 0.1% |
| E: | |
| $C_{12}/C_{15}$ alkyl benzoate marketed under the trademark "Finsolv TN" by Stéarineries Dubois | 4% |
| F: | |
| Purified water | qs 100% |

This cream-gel was prepared in the following manner: the "Pemulen TR1" neutralized with triethanolamine was first dispersed in the "Finsolv TN" (preparation of phase $O_1$ according to the invention). The aqueous phase was then prepared by dissolving D in F. Phase $O_2$ according to the invention was then prepared in the same manner as in Example 1 ($B_1+B_2+B_3$). Phase $O_1$ was introduced into the aqueous phase with stirring. C was added at about 70° C. The mixture was cooled to 40° C. and phase $O_2$ as prepared above was introduced. Lastly, the mixture was cooled to 20° C.

This cream-gel had a particularly high SPF and was very water-resistant.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological composition suited for the photoprotection of human skin and/or hair, comprising (i) a continuous aqueous dispersing phase, (ii) a first discontinuous globular oily dispersed phase $O_1$, (iii) a second discontinuous globular oily dispersed phase $O_2$, (iv) at least one O/W emulsifying agent, (v) at least one W/O emulsifying agent, (vi) a photoprotecting effective amount of at least one lipophilic UV screening agent, (vii) a photoprotecting effective amount of at least one hydrophilic UV screening agent, said first and second oily phases $O_1$ and $O_2$ being mutually incompatible, and the globules constituting said oily phase $O_1$ having an average size which is different from the globules constituting said oily phase $O_2$, which composition is prepared by a process of formulation which comprises intimately admixing into an oil-in-water emulsion prepared by mixing (i) an aqueous phase A and (ii) an oily phase $O_1$ comprising an O/W emulsifying agent, an oily phase $O_2$ comprising a W/O emulsifying agent, at least one lipophilic UV-screening agent, and at least one hydrophilic UV-screening agent; said oily phases $O_1$ and $O_2$ being mutually incompatible.

2. The cosmetic/dermatological composition as defined by claim 1, further comprising a topically applicable, cosmetically and/or dermatologically acceptable vehicle, diluent or carrier therefor.

3. The cosmetic/dermatological composition as defined by claim 1, said at least one W/O emulsifying agent comprising said oily phase $O_2$ and being selected from among dimethicone copolyols and esters thereof.

4. The cosmetic/dermatological composition as defined by claim 1, said at least one hydrophilic UV screening agent comprising a benzophenone compound, a p-aminobenzoic acid compound, a camphor compound or a benzimidazole compound.

5. The cosmetic/dermatological composition as defined by claim 4, wherein said at least one hydrophilic UV screening agent is a camphor compound.

6. The cosmetic/dermatological composition as defined by claim 5, wherein said at least one hydrophilic UV screening agent is benzene-1,4-di(3-methylidene-10-camphorsulfonic) acid.

7. The cosmetic/dermatological composition as defined by claim 4, said at least one hydrophilic UV screening agent comprising a benzimidazole compound.

8. The cosmetic/dermatological composition as defined by claim 7, wherein said at least one hydrophilic UV screening agent is 2-phenylbenzimidazole-5-sulfonic acid.

9. The cosmetic/dermatological composition as defined by claim 1, said at least one hydrophilic UV screening agent comprising from 0.1% to 20% by weight thereof.

10. The cosmetic/dermatological composition as defined by claim 9, said at least one hydrophilic UV screening agent comprising from 0.2% to 10% by weight thereof.

11. The cosmetic/dermatological composition as defined by claim 1, said at least one lipophilic UV screening agent comprising a dibenzoylmethane compound, a benzimidazole compound, a cinnamic compound, a salicylic compound, a camphor compound, a triazine compound, a benzophenone compound, a β,β-diphenylacrylate compound, a p-aminobenzoic acid compound, a screening polymer or a screening silicone.

12. The cosmetic/dermatological composition as defined by claim 11, said at least one lipophilic UV screening agent comprising a dibenzoylmethane compound.

13. The cosmetic/dermatological composition as defined by claim 12, wherein said at least one lipophilic UV screening agent is 4-tert-butyl-4'-methoxydibenzoylmethane.

14. The cosmetic/dermatological composition as defined by claim 11, wherein said at least one lipophilic UV screening agent is a β,β-diphenylacrylate compound.

15. The cosmetic/dermatological composition as defined by claim 14, wherein said at least one lipophilic UW screening agent is 2-ethylhexyl α-cyano-β,β-diphenylacrylate.

16. The cosmetic/dermatological composition as defined by claim 1, said at least one lipophilic UV screening agent comprising from 0.5% to 30% by weight thereof.

17. The cosmetic/dermatological composition as defined by claim 16, said at least one lipophilic UV screening agent comprising from 0.2% to 20% by weight thereof.

18. The cosmetic/dermatological composition as defined by claim 1, said oily phase $O_2$ comprising at least one silicone.

19. The cosmetic/dermatological composition as defined by claim 18, said at least one silicone comprising a volatile silicone.

20. The cosmetic/dermatological composition as defined by claim 18, said at least one silicone comprising from 1% to 20% by weight thereof.

21. The cosmetic/dermatological composition as defined by claim 20, said at least one silicone comprising from 2% to 10% by weight thereof.

22. The cosmetic/dermatological composition as defined by claim 1, further comprising metal oxide nanopigments.

23. The cosmetic/dermatological composition as defined by claim 1, said oily phase $O_1$ being devoid of any UV screening agent.

24. The cosmetic/dermatological composition as defined by claim 1, said aqueous phase being devoid of any UV screening agent.

25. The cosmetic/dermatological composition as defined by claim 1, said oily phase $O_2$ comprising each of said lipophilic/hydrophilic UV screening agents.

26. A process for the formulation of the cosmetic/dermatological composition as defined by claim 1, which comprises intimately admixing, into an oil-in-water emulsion prepared by mixing (i) an aqueous phase A and (ii) said oily phase $O_1$ comprising said at least one O/W emulsifying agent, said oily phase $O_2$ comprising said at least one O/W emulsifying agent, said at least one lipophilic UV screening agent and said at least one hydrophilic UV screening agent, and said oily phases $O_1$ and $O_2$ being mutually incompatible.

27. A regime for protecting human skin and/or hair against the deleterious effects of ultraviolet irradiation, comprising topically applying thereto an effective amount of the cosmetic/dermatological composition as defined by claim 1.

28. A regime for protecting human skin and/or hair against the deleterious effects of solar radiation, comprising topically applying thereto an effective amount of the cosmetic/dermatological composition as defined by claim 1.

* * * * *